(12) United States Patent
Holenstein et al.

(10) Patent No.: US 8,778,281 B2
(45) Date of Patent: Jul. 15, 2014

(54) SAMPLE PREPARATION DOSING UNIT

(75) Inventors: Tobias Holenstein, Kuessnacht am Rigi (CH); Thomas Engel, Buonas (CH); Thomas Sidler, Huenenberg (CH); Adelrich Zuppiger, Siebnen (CH); Carsten Haack, Huenenberg See (CH); Alessandro D'Amore, Wohlen (CH); Michael Meyberg, Rotkreuz (CH); Tobias Greuter, Lucerne (CH); Roland Stoeckli, Boswil (CH)

(73) Assignee: Roche Diagnostics Operations, Inc, Indianapolis, IN (US)

( * ) Notice: Subject to any disclaimer, the term of this patent is extended or adjusted under 35 U.S.C. 154(b) by 770 days.

(21) Appl. No.: 12/849,840

(22) Filed: Aug. 4, 2010

(65) Prior Publication Data

US 2011/0030803 A1 Feb. 10, 2011

(30) Foreign Application Priority Data

Aug. 4, 2009 (EP) .................................... 09167174

(51) Int. Cl.
*B01L 3/02* (2006.01)
*G01N 35/10* (2006.01)
*G01N 1/38* (2006.01)

(52) U.S. Cl.
CPC ............ *G01N 35/10* (2013.01); *G01N 35/1002* (2013.01); *G01N 1/38* (2013.01); *G01N 35/1065* (2013.01)
USPC ............................. 422/509; 422/515; 422/522

(58) Field of Classification Search
CPC ..... G01N 35/10; G01N 1/38; G01N 35/1002; G01N 35/1065

USPC ......................................... 422/509, 515, 522
See application file for complete search history.

(56) References Cited

U.S. PATENT DOCUMENTS

| 2,683,418 | A | 7/1954 | Smith |
|---|---|---|---|
| 5,261,234 | A | 11/1993 | Holloway et al. |
| 5,474,744 | A | 12/1995 | Lerch |
| 6,656,724 | B1 | 12/2003 | Heimberg et al. |
| 2004/0028565 | A1 | 2/2004 | Abou-Saleh et al. |
| 2006/0211132 | A1* | 9/2006 | Miledi et al. .................. 436/180 |
| 2010/0310765 | A1* | 12/2010 | Olsson et al. .............. 427/207.1 |

FOREIGN PATENT DOCUMENTS

| WO | 02086327 A1 | 10/2002 |
|---|---|---|
| WO | 2005080606 A1 | 9/2005 |

* cited by examiner

*Primary Examiner* — Jill Warden
*Assistant Examiner* — Brittany Fisher
(74) *Attorney, Agent, or Firm* — Roche Diagnostics Operations, Inc.

(57) ABSTRACT

A sample preparation dosing unit for liquid dosing is provided comprising an inlet port and an outlet port fluidically coupling the sample preparation dosing unit to a supply and target, respectively; a pump, fluidically arranged between the inlet port and the outlet port; an outlet flow restrictor with an outlet flow resistance, fluidically arranged between a pump outlet and outlet port; and a control arrangement with a branch, a control valve, and a control flow restrictor with a control flow resistance. The branch divides the flow at the pump outlet into an outlet flow through the outlet flow restrictor and into a control flow through the control flow restrictor. The control flow downstream of the control flow restrictor is fed, depending on the state of the control valve, either into the outlet port thereby merging with the outlet flow downstream of the outlet flow restrictor, or into a bypass conduit.

14 Claims, 3 Drawing Sheets

SAMPLE PREPARATION DOSING UNIT

BACKGROUND OF THE INVENTION

The present invention is related to the technical field of liquid dosing, in particular to sample preparation dosing units, to sample preparation devices comprising such dosing units as well as to corresponding methods for liquid dosing in sample preparation devices.

The application WO 99/26070 discloses the usage of two separate pumps which are designed for different flow rates and used for alternatively dosing chemical reagents or a cleaning liquid.

The application US 2004/0028565A1 discloses an arrangement with two coupled piston pumps and controlled valves for sequentially dosing a reagent and a cleaning liquid. This design, however, is complex and restricted to carrying out cycles of dosing reagent, followed by subsequent cleaning.

SUMMARY OF THE INVENTION

It is against the above background that the present invention provides certain unobvious advantages and advancements over the prior art. In particular, the inventors have recognized a need for improvements in sample preparation dosing units and in sample preparation devices comprising such dosing units, as well as to corresponding methods for liquid dosing in sample preparation devices.

Although the present invention is not limited to specific advantages or functionality, it is noted that the present invention provides sample preparation dosing units which are flexible and provide both high and low flow rates with a single pump. In other aspects, the invention further provides probe preparation devices which comprise such dosing units as well as corresponding liquid dosing methods.

In accordance with one embodiment of the present invention, a sample preparation dosing unit for liquid dosing from a supply to a target in a sample preparation device is provided, comprising: an inlet port for fluidically coupling the sample preparation dosing unit to the supply; an outlet port for fluidically coupling the sample preparation dosing unit to the target; a pump, fluidically arranged between the inlet port and the outlet port; an outlet flow restrictor with an outlet flow resistance, fluidically arranged between an outlet of the pump and the outlet port; and a control arrangement with a branch, a control valve and a control flow restrictor with a control flow resistance. The flow at the outlet of the pump is divided by the branch into an outlet flow through the outlet flow restrictor and into a control flow through the control flow restrictor. The control flow downstream of the control flow restrictor is fed, in dependence of the state of the control valve, either into the outlet port such that it merges with the outlet flow downstream of the outlet flow restrictor, or into a bypass conduit.

In accordance with another embodiment of the invention, a method for dosing liquid from a supply to a target in a sample preparation device is provided, comprising: pumping liquid from the supply through a pump into a branch; dividing by the branch the flow downstream of the pump into an outlet flow through an outlet flow restrictor, an outlet of the outlet flow restrictor being fluidically coupled to the target via an outlet port, and into a control flow through a control flow restrictor; and controlling the state of a control valve, the control valve being arranged downstream of the control flow restrictor, to feed the control flow selectively either into the outlet port such that it merges with the outlet flow downstream of the outlet flow restrictor, or into a bypass conduit.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

In the following, exemplary embodiments of the dosing unit and the liquid dosing method as well as a sample preparation device in accordance with various embodiments of the invention are described in more detail with reference to the figures.

Figure 1:
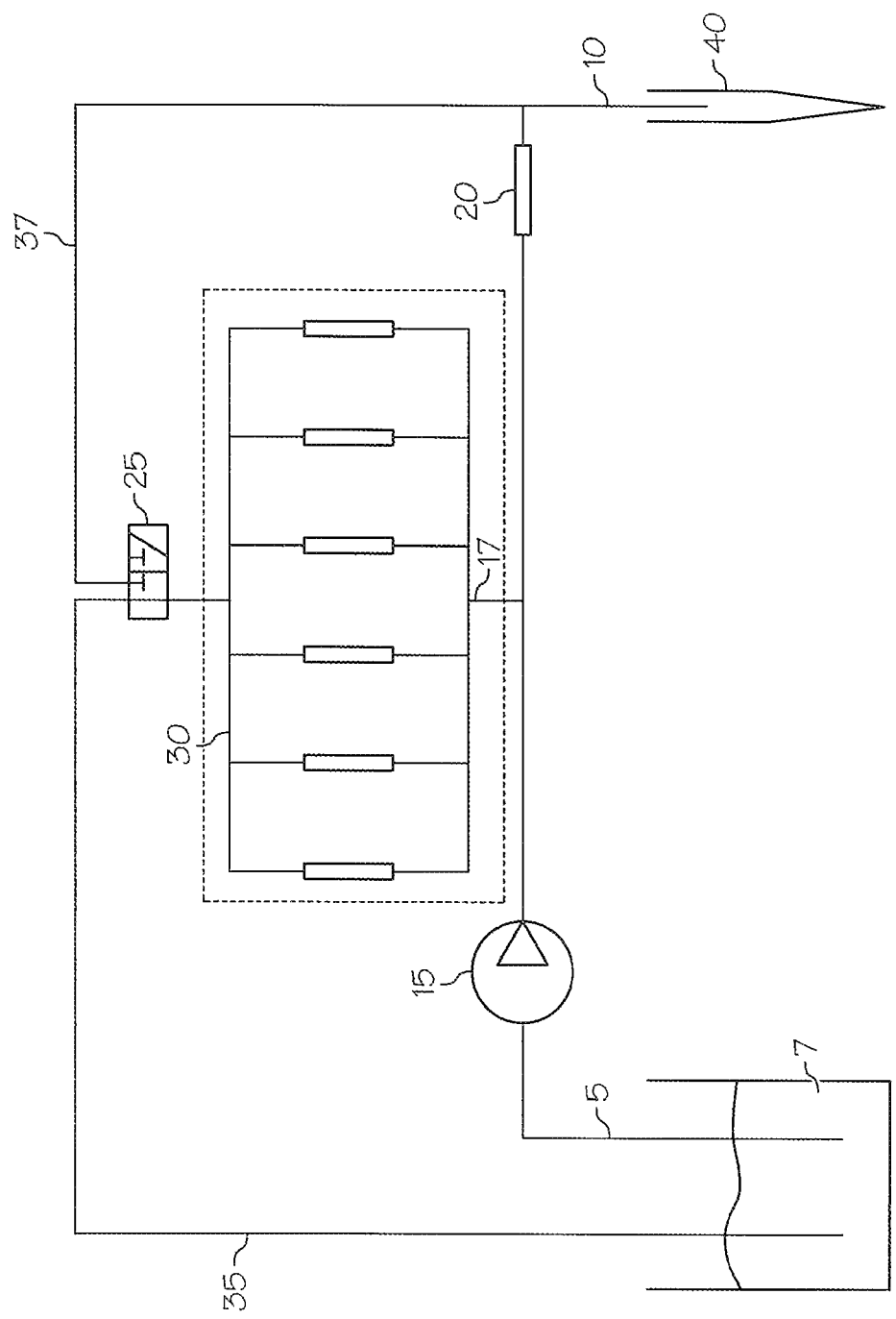
FIG. 1 and FIG. 2 each show an exemplary dosing unit in a schematic and structural view, in accordance with embodiments of the invention.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

Embodiments of the present invention may especially be used in combination with automated analyzers as they are widely known, for example, as chemical, biochemical or genetic analyzers in the fields of medical research and laboratory medicine.

Sample preparation means that adjuvant fluids are combined with original samples to achieve a sample suitable for analysis. The original samples are typically biological samples, in particular blood, urine or tissue samples.

Adjuvant fluids are in particular Lysis buffers, diluents and reagents.

The step of combining original sample with adjuvant fluid is carried out by a device which is herein called a sample preparation device. A central unit of such sample preparation device is a sample preparation dosing unit which has the function of dosing fluids. The sample preparation dosing unit doses adjuvant fluid and may also dose original sample.

The liquid amounts which have to be handled by a sample preparation dosing unit may vary in a large range. Reagents require dosing with small flow rates, e.g., 1 μl/h or even less. Lysis buffers and diluents require considerably higher flow rates, e.g., 1 ml/h or even larger, for dosing in a reasonable time. The ratio of the lowest to the highest required flow rate may be in the range of 1:1000 or even larger.

Between the dosing steps, cleaning with a cleaning liquid may be required at flow which may be in the range of several ml/h.

According to a first aspect, the present invention is directed towards a sample preparation dosing unit which comprises: a) an inlet port for fluidically coupling the sample preparation dosing unit to a supply; b) an outlet port for fluidically coupling the sample preparation dosing unit to a target; c) a pump, fluidically arranged between the inlet port and the outlet port; d) an outlet flow restrictor with an outlet flow resistance, fluidically arranged between an outlet of the pump and the outlet port; e) a control arrangement with a branch, a control valve and a control flow restrictor with a control flow resistance, such that the flow at the outlet of the pump is divided by the branch into an outlet flow through the outlet flow restrictor and into a control flow through the control flow restrictor, and the control flow downstream of the control flow restrictor is fed, in dependence of the state of the control valve, and either into the outlet port such that it merges with the outlet flow downstream of the outlet flow restrictor, or into a bypass conduit.

The liquid delivery to the target is accordingly, at least partly, being controlled via the state of the control valve. The liquid flow may be additionally controlled via the pump as will be discussed later on.

The invention allows one to operate the pump at a flow rate or in a flow rate range which is optimal according to the pump design. Considerably lower flow rates can be achieved by switching the control valve.

A flow restrictor is a component or assembly that limits and restricts the liquid flow by imposing a fluidic resistance to the liquid. The relation between the liquid flow and the pressure drop over the flow restrictor may be proportional, as it is the case, for example, for the laminar flow through a capillary. Alternatively, the relation may be non-proportional as it is the case for many aperture plate assemblies.

The flow restrictors may be made in several ways and typically may be apertures, in particular aperture bores, in an aperture plate, or may be capillaries. For aperture plates, both the control flow restrictor and the outlet flow restrictor are typically made by aperture bores in the same aperture plate. Alternatively, the flow restrictors may, totally or in part, be formed by liquid conduits, such as tubing.

A control valve as used in embodiments of the present invention is a valve with an inlet and at least two outlets, and switches the flow from the inlet to either of the at least two outlets in dependence of its state. The state of the control valve is changed via an actuation assembly such as a motor or electro magnet.

The control valve is designed for electrical or pneumatic actuation via an electronic control unit. The control unit may, for example, be the control unit of a probe preparation device or a general purpose computer, such as a personal computer.

The control valve may be of any design known in the art for the corresponding type of application and may, for example, be a 3-port/2-way valve. Rotary valves have the specific advantage that switching of the valve state is not associated with an undesired liquid displacement due to the movement of the valve body.

The pump may generally be of any design known in the art for the corresponding type of application. The pump may, for example, be a miniaturized piston pump, membrane pump or rotary displacement pump. Generally suited rotary displacement pump are especially micro gear pumps, toothed wheel pumps or peristaltic pumps.

While being comparatively low in weight, micro gear pumps and toothed belt pumps advantageously allow for highly-precise dosing of liquids and enable pipetting operations in a wide range of flow rates. In addition, the pumping direction of those pumps is reversible which is of advantage in a number of further operations carried out by sample preparation devices, in particular pipetting operations.

In order to compensate for the back-flow which is associated with different pump designs, the pump may be back-flow compensated, as disclosed, for example, in the co-pending European patent application No. 09159200.6.

The pump may be operated in an open loop or in a closed loop with feedback being provided by pressure and/or flow sensing.

Assuming substantially equal pressures, for example atmospheric pressure, at both the inlet port and the outlet of the bypass conduit, the ratio of the outlet flow rate, $F_o$, and the control liquid flow rate, $F_c$, equals the ratio of the control flow resistance $R_c$ to outlet flow resistance $R_o$, i.e., $$F_o/F_c = R_c/R_o \qquad (1).$$

If the state of the control valve is such that the control flow merges with the outlet flow, the whole flow with the flow rate $F_o + F_c$ through the pump is delivered to the outlet port. If the state of the control valve is such that the control flow is fed into the bypass conduit, only the smaller liquid flow $F_o$ is delivered to the outlet port. By corresponding dimensions of the outlet flow resistance $R_o$ and the control flow resistance $R_c$, the desired flow ratio may be achieved.

In some typical embodiments, the control flow resistance $R_c$ is small as compared to the outlet flow resistance $R_o$. In this way, the dosing unit can be controlled to deliver liquid to the target with two different flow rates which may have a large ratio, of for example 1:100, 1:1000 or even more. This is favorable, for example, for dosing reagents at a very small rate and dosing other liquids, in particular Lysis buffers, diluents and/or cleaning fluids at a much higher flow rate.

In some of those embodiments, the control flow restrictor comprises a number of sub flow restrictors in a parallel fluidic arrangement, in particular a number of aperture bores. The flow resistance of each of the sub flow restrictors may equal the output flow resistance. For this type of embodiments, all single flow restrictors in the dosing unit have the same flow resistance and may be of the same design, which is especially favorable with respect to manufacturing tolerances of the bores.

In some embodiments, the pump has a variable flow rate and a pump controller is provided for controlling the flow rate. While the state of the control valve is decisive for the distribution of the flow, the total flow rate is given by the flow rate through the pump. By controlling the flow rate through the pump, the rate at which liquid is delivered to the target may accordingly be further controlled. In a corresponding design, a continuous variation of the flow rate may be achieved in this way. If the pump is, for example, a rotary displacement pump, the flow rate through the pump can be controlled by controlling the speed of the pump motor.

Using a speed-controlled pump in a dosing unit according to the present invention allows realizing a large flow range without requiring the pump itself to provide the large flow range. The highest achievable flow rate is given by maximum flow rate of the pump while the lowest achievable flow rate is given by the minimum flow rate of the pump and the relation given by (1). For this design, the maximum flow rate of the pump is still available while the minimum flow rate is lowered. The total flow rate range at which the dosing unit can be operated is accordingly significantly increased by the present invention. The flow rate ranges which may be selected by switching the control valve may be overlapping, adjacent, or show a gap. The pump may be speed-controlled in an open loop or in a closed loop with sensor feedback.

In some embodiments, all liquid-contacting elements of the dosing unit, such as tubing, flow restrictors and the liquid-contacting portions of the control valve and the pump, are removable from the further components and/or replicable, such that they can be easily replaced and/or cleaned.

In some embodiments, the outlet port is designed to couple to a pipette or a pipette tip. The pipette or pipette tip may in some embodiments be replaced independently from the further liquid-contacting components.

In some embodiments, an outlet of the bypass conduit couples, during operation of the dosing unit, to the supply or a discard sink. If the outlet of the bypass conduit couples to the supply, the amount of liquid that is fed into the bypass conduit and is not delivered to the target may be reused. If the supply is, for example, a reagent container, there will be a circular flow from the reagent container, through the inlet port, the pump, the control flow restrictor, the control valve, and, via the bypass conduit, back into the reagent container. Only the amount of liquid that is delivered to the target is taken out of the circular flow. This kind of embodiment is typical if the liquid is an expensive reagent. Alternatively, it may be desired to discard the liquid from the bypass conduit into a discard container, a drain, or the like. In a further variant, the outlet of the bypass conduit may alternatively couple to the supply or a discard sink.

In some embodiments, the dosing unit couples to or comprises a selecting assembly which may be controlled for
fluidically coupling the inlet port (5) alternatively to at least two different supplies, and/or
for fluidically coupling the outlet port (10) to at least two different targets, in dependence of the state of the selecting assembly.

In this way, liquid may be taken from a variety of supplies and/or dosed to a variety of targets.

In typical sample preparation devices, a number of different supplies are provided, such as Lysis buffer, diluents, cleaning liquid and different reagents. The corresponding selecting assembly is typically realized by a valve arrangement with a number of electrically controlled switching valves and/or a manifold valve. The selecting arrangement may be designed such that the outlet of the bypass conduit is fluidically coupled the selected supply.

At least two targets may, for example, be different samples and a discard sink for cleaning liquid. For this purpose, the selecting arrangement may comprise a positioning system coupled to the inlet port and/or the outlet port for positioning the inlet port to couple with either of the supplies and/or to position the outlet port to couple to either of the targets. A positioning system may, for example, be based on a Cartesian robot, a SCARA robot or any other kinematics in dependence of the application.

In an analogue way, a valve arrangement may be used to couple the outlet port to a number of different targets and/or a positioning system may be used to couple the inlet port to a number of different sources.

The embodiments described so far allow switching the flow rate of the flow that is delivered to the target between two values in dependence of the state of the control valve with further control being optionally available by controlling the pump. However, a sample preparation dosing unit in accordance with an embodiment of the invention may also be designed for switching between several different flow rates for a given flow rate of the pump.

In this type of embodiment, the control arrangement comprises a set of N control flow restrictors and a set of corresponding N control valves such that
the flow at the outlet of the pump is divided by the branch into the outlet flow through the outlet flow restrictor and a number of N control flows through the N control flow restrictors, and each of the N control flows is selectively fed, in dependence of the state of the corresponding control valve
either into the outlet port such that it merges with the outlet flow downstream of the outlet flow restrictor
or into the bypass conduit.

Because each control flow is reciprocally proportional to the corresponding control flow resistance, the relation given by (1) holds true for the flow distribution between the single control flow restrictors in an analogues way.

The control flow resistances of each of the set of control flow restrictors may be identical or different. Since the flow through each of the control valves is determined by the corresponding control flow resistance, this kind of embodiment allows coarse as well as fine adjustment of the flow that is delivered to the target with a relatively small number of valves and control flow restrictors.

Small flow resistances can typically be achieved by a parallel fluidic arrangement of a number of identical sub flow restrictors, in particular a number of identical aperture bores or a number of identical capillaries.

The single control valves may be separate components or may be integrated to form a single compact valve unit.

In combination with a pump which allows varying the flow rate in a certain range, a liquid dosing module may be designed which allows selecting between a number of flow rate ranges for the delivery to the target and controlling the rate flow within the single ranges via the flow rate of the pump.

According to a further aspect, the invention is directed towards a sample preparation device, as that typically used in combination with a medical or chemical analyzer, which comprises a sample preparation dosing unit in accordance with the invention. The further components as well as the overall architecture of the sample preparation device may be designed in accordance with the state of the art.

In accordance with a still further aspect, the invention is directed towards a liquid dosing method from a supply to a target. The method comprises the steps of:
a) pumping liquid from the supply through a liquid pump into a branch,
b) dividing by the branch the flow downstream of the pump into an outlet flow through an outlet flow restrictor, an outlet of the outlet flow restrictor being fluidically coupled to the target via an outlet port, and into a control flow through a control flow restrictor,
c) controlling the state of a control valve, the control valve being arranged downstream of the control flow restrictor selectively
either into the outlet port such that it merges with the outlet flow downstream of the outlet flow restrictor
or into a bypass conduit.

The method may typically be carried out with a sample preparation dosing unit in accordance with an embodiment of the invention as described above and will be further described below in exemplary embodiments.

Specific and exemplary embodiments of the liquid dosing method may be derived from embodiments of the sample preparation dosing unit in a straight-forward way.

With reference to FIG. 1, the unit comprises an inlet port 5 which is fluidically coupled to the reagent container 7 from which it may take up liquid reagent. In the shown embodiment, the reagent container 7 has an open top side. An end portion of the inlet port 5 dips into the liquid within the reagent container 7. Alternative ways of coupling, however, may be used as well.

An input selecting arrangement for selectively coupling the input port to a number of sources is not be shown for clarity reasons, but is typically present as well and may be designed in accordance with the state of the art.

The inlet port 5 couples to the inlet of the pump 15 which is designed as micro toothed wheel pump. The pump outlet is coupled to an outlet port 10 via an outlet flow restrictor 20.

The outlet port 10 is fluidically coupled to a replaceable pipette or pipette tip 40. By operating the pump 15, liquid may accordingly be delivered from the reagent container 7 to the outlet of the pipette 40 via the outlet flow restrictor 20. In addition, sensors, in particular flow and/or pressure sensors may be present as well for closed-loop control of the pump 15.

Via the tip of the pipette 40, the liquid can be dosed to a target, such as a blood or tissue sample (not shown).

Between the outlet of the pump 15 and the inlet of the outlet flow restrictor 20, a portion of the flow is branched-off in the branch 17 into a control flow restrictor 30. The control flow restrictor 30 is exemplarily shown as a set of sub flow restrictors in a parallel fluidic arrangement.

The outlet of the control flow restrictor 30 is coupled to the inlet of a control valve 25 which is exemplarily realized as 3-port/2-way valve.

The fluidic resistance of the control flow restrictor 30 is designed to be considerably smaller as compared to the outlet flow restrictor 20. In dependence of the state of the control valve 25, the control flow either merges with the outlet flow downstream of the outlet flow restrictor 20 and upstream of the inlet of the pipette 40 via a forwards feeding conduit 37, or is fed into a bypass conduit 35. The latter situation is shown in FIG. 1.

In the shown example, liquid which is fed into the bypass conduit 35 is returned into the reagent container 7. Alternatively, it may be fed into a discard sink, such as a discard liquid container.

For each state of the control valve 25, the inactive of the bypass conduit 35 and the forwards feeding conduit 37, respectively, is closed by the control valve 25.

Both the pump 15 and the control valve are electrically controlled via an electronic control unit (not shown), such as the control unit of a chemical or medical analyzer, a general-purpose, computer, or the like.

Figure 2:
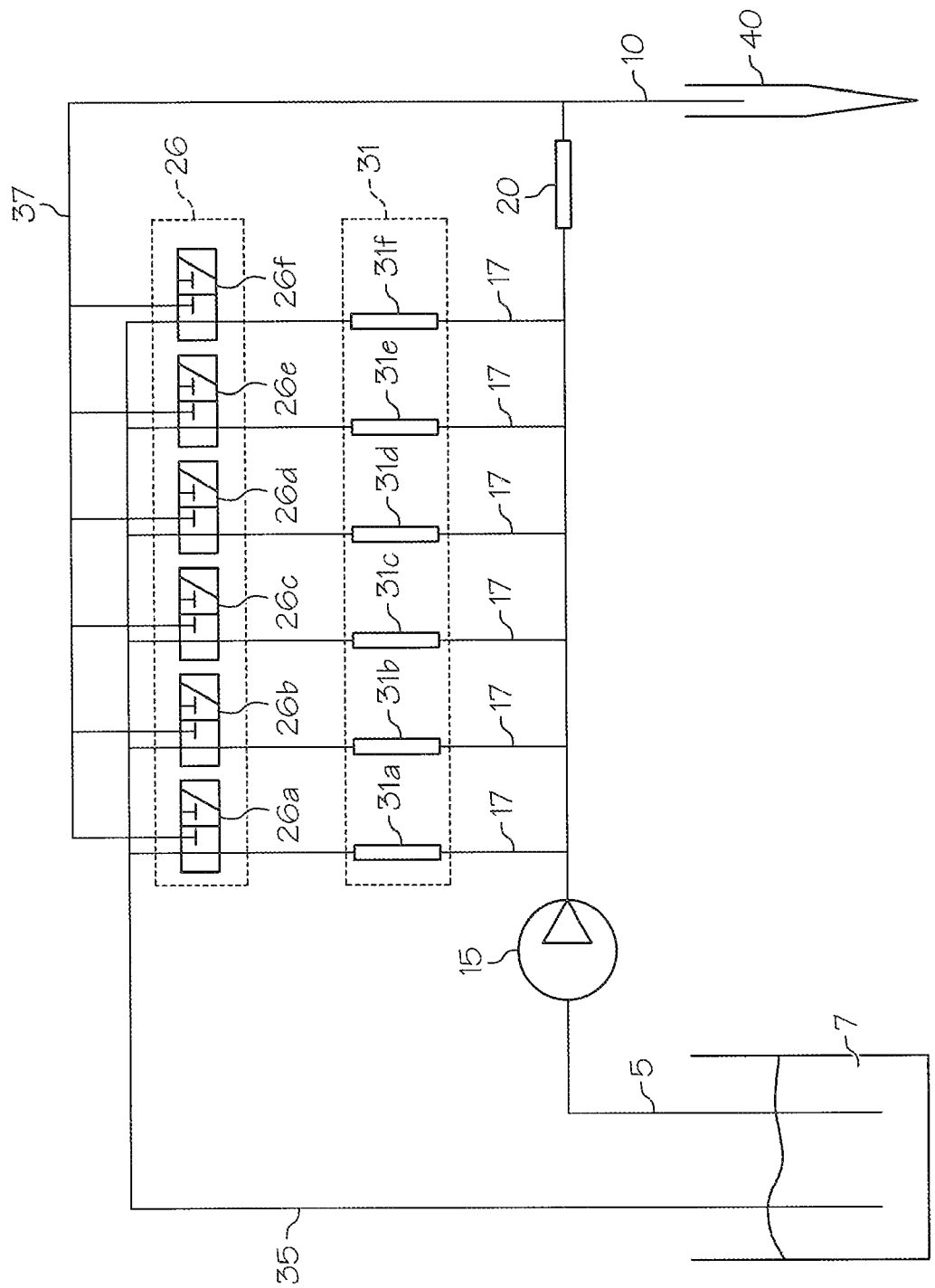

For the further exemplary dosing unit which is shown in FIG. 2, the basic principle of operation is in accordance with the previously described embodiment. Several of the structural elements of this further exemplary embodiment may be designed in substantially the same way as in the previously described embodiment and fulfill the same function. Those elements are indicated by identical reference numbers. The following description is focused on those elements and aspects which are specific for this further embodiment.

Instead of a single control flow restrictor 30 (see FIG. 1), a set of independent control flow restrictors, 31a, 31b, 31c, 31d, 31e, 31f is provided, each being associated with a corresponding control flow resistance. The outlet of each control flow restrictor 31a . . . 31f is coupled to the inlet of a corresponding control valve 26a, 26b, 26c, 26d, 26e, 26f. The state of each of these control valves is individually controlled by an electronic control unit (not shown).

In dependence of the state of the control valves 26a . . . 26f, each control flow is individually either merged with the outlet flow via the forwards feeding conduit 37 or fed into the bypass conduit 35 as described above.

The control flow restrictors 31a . . . 31f are advantageously made by an aperture plate with bores as described above.

In the embodiment shown in FIG. 2, the branch 17 is designed such that the flow through the control flow restrictors 31a . . . 31f is individually branched-off between the outlet of pump 15 and the inlet of outlet flow restrictor 20. Similarly, the flow is individually fed into the bypass conduit 35 or the forwards feeding conduit 37 downstream of the control valves 26a . . . 26f. Alternatively, the liquid flow through the control flow restrictor 31a . . . 31f may be branched-off commonly and distributed between the single flow restrictors later on. Similarly, the feeding into the forwards feeding conduit 37 and the bypass conduit 35 may be performed in common.

Figure 3:
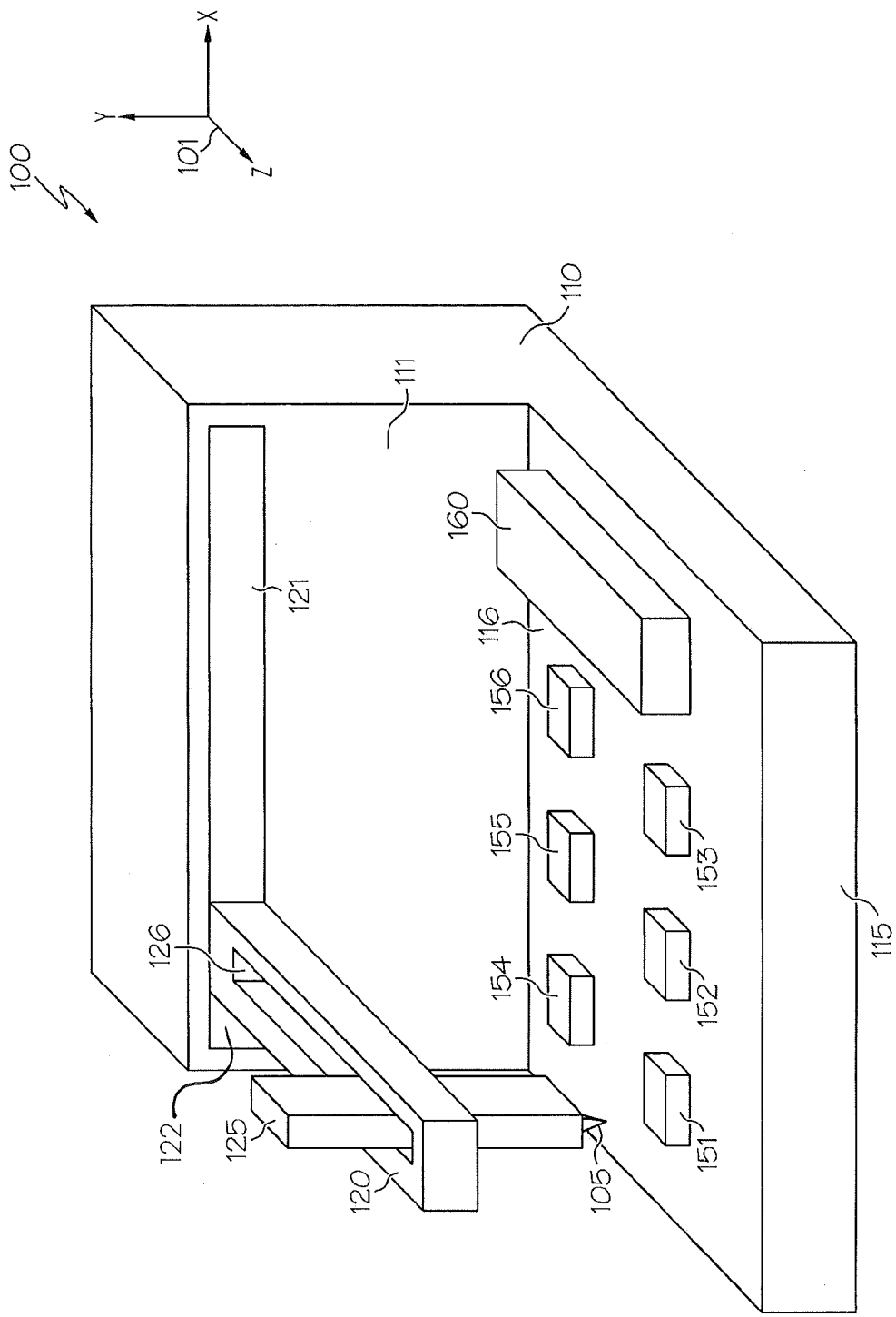
FIG. 3 schematically shows a section of a sample preparation device which comprises a dosing unit in accordance with another embodiment of the present invention.

FIG. 3 shows a section of a sample preparation device 100 in accordance with an embodiment of the present invention. The device comprises a positioning system 122 with an x-arm 120 and an y-z-arm 125. The housing of the device 100 comprises a vertical housing section 110 which has a surface 111 in the x-y plane of a Cartesian system 101 and an horizontal housing section 115 which has a surface 116 in the z-x plane. A number of targets 151, 152, 153, 154, 155, 156 as well as a discard container 160 are located at different positions on the surface 116. The targets 151, 152, . . . 156 are plates or containers typically with biological samples.

The x-arm 120 projects out of a slit 121 in the surface 111 and can be displaced in the x-direction within the slit 121 by an actuator system (not visible) comprised by the housing 110. In a similar way, the y-z-arm 125 can be displaced within a slit 126 of the x-arm 120 in the z-direction and can be moved upwards and downwards in the y-direction.

The y-z arm 125 carries a pipette tip 105 which is coupled to the outlet port of the liquid dosing unit. The positioning system 122 allows the pipette tip 105 to be aligned with either of the targets 151, 152, . . . 156 or the discard sink 160. Fluidic coupling with each of the targets 151, 152, . . . 156 can be achieved by moving the y-z arm downwards in the -y direction. In order to avoid cross-contamination, the y-z arm is advantageously controlled such that the pipette tip does not mechanically contact the target. For positioning, the y-z arm 125 is moved upwards in the y-direction.

The control arrangement and the pump are comprised by the housing 110 and are therefore not visible in FIG. 3. The housing 110 further comprises a number of supplies in form of a reagents kit. Lysis buffer, diluents and cleaning liquid are provided in larger containers (not shown) below the device. A valve-based supply selecting arrangement (not visible) is further comprised by the housing 110 for selecting either of the supplies and simultaneously coupling the outlet of the bypass conduit to the selected supply. If the liquid is cleaning liquid, however, it may be typical to couple the outlet of the bypass conduit to the discard container 160 or another discard sink, in order to avoid contamination of the cleaning fluid in the cleaning fluid container.

The tubing (not visible) of the pipette tip 105 and the other fluidic components is made by elastic tubes which have a cross sectional area of negligible flow resistance.

The actuators of the positioning system 122, the pump, the control valve and the supply selecting arrangement are controlled via an electronic controller unit which is typically computer based and may be comprised by the housing 110, further sections of the analyzer (not shown), or may be external.

The valve arrangement of the supply selecting assembly is typically operatively coupled to the control valve such that both valves can be switched together. The valves are controlled in the following way. If the state of the assembly is such that the source is Lysis buffer, diluents or cleaning liquid, the state of the control valve is such that the flow through the control flow restrictor merges with the flow through the outlet flow restrictor, resulting in a high flow. If the state of the supply selecting assembly is such that either of the reagents serves as source, the state of the selecting valve is such that the flow through the control flow restrictor is fed into the bypass conduit, resulting in the flow to be low.

It should be noted that the arrangement of FIG. 3 is exemplary and may be varied in a number of ways. For example, the kinematics of the positioning system 122 may also be modified in a number of ways. For example, the targets 151, 152, . . . 156 may be arranged on a rotary table. In this case, a single degree of freedom, for example in the y-direction, may be sufficient for the pipette tip 105. Additionally or alternatively to a positioning system, multiple dosing units may be present for parallel dosing to a number of targets.

It is noted that terms like "preferably", "commonly", "favorably", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined by the appended claims. More specifically, although some aspects of the present invention are identified herein as preferred or particularly advantageous, it is contemplated that the present invention is not necessarily limited to these preferred aspects of the invention.

What is claimed is:

1. A sample preparation dosing unit for liquid dosing from a supply to a target in a sample preparation device, comprising:
    an inlet port for fluidically coupling the sample preparation dosing unit to the supply;
    an outlet port for fluidically coupling the sample preparation dosing unit to the target;
    a pump, fluidically arranged between the inlet port and the outlet port;
    an outlet flow restrictor with an outlet flow resistance, fluidically arranged between an outlet of the pump and the outlet port; and
    a control arrangement with a branch, a control valve and a control flow restrictor with a control flow resistance, such that
    the flow at the outlet of the pump is divided by the branch into an outlet flow through the outlet flow restrictor and into a control flow through the control flow restrictor, and the control flow downstream of the control flow restrictor is fed, depending on the state of the control valve either
    into the outlet port such that it merges with the outlet flow downstream of the outlet flow restrictor, or
    into a bypass conduit.

2. The sample preparation dosing unit in accordance with claim 1, wherein during operation of the sample preparation dosing unit the outlet port is coupled to a pipette or pipette tip.

3. The sample preparation dosing unit in accordance with claim 1, wherein the control flow resistance is less than the outlet flow resistance.

4. The sample preparation dosing unit in accordance with claim 3, wherein the control flow restrictor comprises a number of sub flow restrictors in a parallel fluidic arrangement.

5. The sample preparation dosing unit in accordance with claim 4, wherein the flow resistance of each of the sub flow restrictors is equal to the outlet flow resistance.

6. The sample preparation dosing unit in accordance with claim 1, wherein the control arrangement further comprises a set of N control flow restrictors and a set of corresponding N control valves, such that
    the flow downstream of the pump is divided by the branch into the outlet flow through the outlet flow restrictor and a number of N control flows through the N control flow restrictors, and the control flow downstream of each of the control flow restrictors is selectively fed, depending on the state of the corresponding control valve either
    into the outlet port such that it merges with the outlet flow downstream of the outlet flow restrictor, or
    into the bypass conduit.

7. The sample preparation dosing unit in accordance with claim 1, wherein during operation of the sample preparation dosing unit the inlet port is coupled to a reagent container and/or a cleaning liquid container.

8. The sample preparation dosing unit in accordance with claim 1 further comprising a supply selecting arrangement which may be controlled for fluidically coupling the inlet port alternatively to at least two different supplies, and/or for fluidically coupling the outlet port to at least two different targets, in dependence of the state of the selecting assembly.

9. The sample preparation dosing unit in accordance claim 8, wherein the supply selecting arrangement comprises at least one of
    a positioning system coupled to the inlet port and/or the outlet port for positioning the inlet port to couple with either of the supplies and/or to position the outlet port to couple to either of the targets, or
    a selecting valve coupled to the inlet port and/or the outlet port for coupling the inlet port with either of the supplies and/or coupling the outlet port with either of the targets, in dependence of the state of the selecting valve.

10. The sample preparation dosing unit in accordance with claim 1, wherein during operation of the sample preparation dosing unit an outlet of the bypass conduit is coupled to the supply or a discard sink.

11. The sample preparation dosing unit in accordance with claim 1, wherein the pump comprises a variable flow rate, and which unit further comprises a pump controller for controlling the flow rate.

12. A method for dosing liquid from a supply to a target in a sample preparation device, comprising the steps of:
    pumping liquid from the supply through a pump into a branch;
    dividing by the branch the flow downstream of the pump into an outlet flow through an outlet flow restrictor, an outlet of the outlet flow restrictor being fluidically coupled to the target via an outlet port, and into a control flow through a control flow restrictor; and
    controlling the state of a control valve, the control valve being arranged downstream of the control flow restrictor, to feed the control flow selectively either
    into the outlet port such that it merges with the outlet flow downstream of the outlet flow restrictor, or
    into a bypass conduit.

13. The method for dosing liquid according to claim 12, further comprising
    dividing by the branch the flow downstream of the pump outlet into the outlet flow and a number of N control flows through N corresponding control flow restrictors; and controlling the state of N control valves, the N control valves being arranged downstream of the N control flow restrictors, to selectively feed each of the N control flows either into the outlet port such that it merges with the outlet flow downstream of the outlet flow restrictor, or into a bypass conduit.

14. The method for dosing liquid according to claim 12, further comprising selecting the supply as either of at least two different supplies; and controlling the control valve such that the control flow merges with the output flow if the supply is selected as a first one of the at least two supplies and is fed into the bypass conduit if the supply is selected as a second one of the at least two supplies.

\* \* \* \* \*